(12) United States Patent
Bonnevie

(10) Patent No.: US 8,790,624 B2
(45) Date of Patent: Jul. 29, 2014

(54) METHOD FOR ADDING ACTIVE INGREDIENTS TO A NAIL VARNISH AND NAIL VARNISH THUS PREPARED

(75) Inventor: Xavier Bonnevie, Mainvilliers (FR)

(73) Assignee: Fiabila, Mainton (FR)

( * ) Notice: Subject to any disclaimer, the term of this patent is extended or adjusted under 35 U.S.C. 154(b) by 173 days.

(21) Appl. No.: 13/505,887

(22) PCT Filed: Nov. 5, 2010

(86) PCT No.: PCT/FR2010/052384
§ 371 (c)(1),
(2), (4) Date: May 3, 2012

(87) PCT Pub. No.: WO2011/058266
PCT Pub. Date: May 19, 2011

(65) Prior Publication Data
US 2012/0213718 A1 Aug. 23, 2012

(30) Foreign Application Priority Data
Nov. 10, 2009 (FR) ...................................... 09 05388

(51) Int. Cl.
*A61Q 3/00* (2006.01)
*A61K 8/67* (2006.01)
*A61K 8/06* (2006.01)
*A61Q 3/02* (2006.01)
*A61K 8/39* (2006.01)
*A61K 8/894* (2006.01)

(52) U.S. Cl.
CPC ... *A61K 8/06* (2013.01); *A61Q 3/02* (2013.01); *A61K 8/39* (2013.01); *A61K 8/894* (2013.01); *A61K 2800/52* (2013.01)
USPC ........................................................... 424/61

(58) Field of Classification Search
USPC ........................................................ 424/61
See application file for complete search history.

(56) References Cited

U.S. PATENT DOCUMENTS

| | | |
|---|---|---|
| 5,102,654 A | 4/1992 | Castrogiovanni et al. |
| 5,484,586 A | 1/1996 | Bedard |
| 2008/0139453 A1 | 6/2008 | Yoshimi et al. |

FOREIGN PATENT DOCUMENTS

| | | |
|---|---|---|
| FR | 2819401 | 7/2002 |
| WO | 9641612 | 12/1996 |

OTHER PUBLICATIONS

International search report dated Apr. 6, 2011 in corresponding PCT/FR2010/052384.

*Primary Examiner* — Gina C Justice
(74) *Attorney, Agent, or Firm* — Young & Thompson

(57) ABSTRACT

A method for adding active agents to a nail varnish, in emulsion form. The method is suitable for adding active agents by minimizing the breakdown of same in the varnish, or the destabilization of the varnish. The method also enables the addition of active ingredients that were previously incompatible with the varnish medium.

16 Claims, No Drawings

METHOD FOR ADDING ACTIVE INGREDIENTS TO A NAIL VARNISH AND NAIL VARNISH THUS PREPARED

The present invention relates to the field of nail polish, and more particularly to a method of incorporating active agents into nail polish compositions.

Conventionally, nail polish compositions are based on solvent(s). They generally comprise:
- a film-forming agent, normally nitrocellulose or a nitrocellulose derivative;
- a plasticizer;
- sometimes, a thixotropic agent;
- at least one resin; and
- one or more solvents;
- coloring agents and/or pigments.

More recently, nail polishes have been developed that are based on an aqueous phase. They comprise:
- a film-forming agent such as an acrylic or styrene acrylic binder;
- one or more coalescing agents;
- one or more plasticizers;
- water;
- coloring agents and/or pigments;
- thickening agents and thixotropic agents.

For particular applications, for example to strengthen the nail or to hydrate it, such nail polishes may include as additives agents that have an action on the nail, such as hydrating agents or nail hardening agents.

Such compounds may degrade when the composition is stored or during application to the nail. Certain of said additives may also destabilize the nail polish and reduce its properties, such as hardness, gloss, etc., even though they are introduced in small quantities. The majority of those compounds can be incorporated in the nail polish composition in small quantities only, usually because they are either incompatible with the solvent for the nail polish, or because their solubility in it is very low, meaning that they are difficult to integrate into the nail polish composition.

It has been possible to introduce certain specific active agents into the nail polish compositions by adding specific stabilizers for the active molecule; as an example, in patent EP 0 931 538, N-chlorosuccinimide or boric acid is added, or in U.S. Pat. No. 4,897,261, high molecular weight (>1000) polymers comprising a hydrophilic portion and a lipophilic portion are introduced.

The principal aim of the present invention is thus to overcome the above disadvantages by proposing a method of preparing a nail polish composition that is simple, that is capable of being carried out at ambient temperature, and that incorporates agents with an action on the nail, which can protect said active agents in said nail polish composition without adding either acid or polymer as is described in the prior art documents.

To this end, the invention provides a method of incorporating an agent with an action on the nail of the mineral salt and/or organic compound type, such as a vitamin, a plant extract, essential oils, into a nail polish composition comprising a film-forming agent with a view to preserving the agent, the method being characterized in that it comprises the following steps in succession:

a) preparing an oil-in-water or water-in-oil type emulsion by bringing at least one first phase constituted by said active agent or a solution dissolving it into contact, with stirring, with a second phase in which the agent is insoluble or slightly soluble, in the presence of at least one surfactant, in order to obtain a simple, stable emulsion constituted by two phases, the first, discontinuous phase being present in the form of droplets in the second, continuous phase, said second phase being soluble in the polish composition;

b) then introducing, with stirring, said emulsion into a polish composition in proportions in the range 0.01% to 5% of the composition weight.

Thus, the agent with an action on the nail is present in a phase that is immiscible with the solvent for said polish and/or in a phase that is distinct from the solvent phase for said polish, so that it is protected during storage of the polish and released in contact with the nail when the polish is applied to the nail.

The respective proportions by weight of the phases of the emulsion are advantageously in the range approximately 20-80 to 80-20, preferably in the range 35-65 to 65-35.

Advantageously, in accordance with the invention, it is also possible to provide the method with a step a)bis in which the simple emulsion obtained at the end of step a) is incorporated, with stirring, before step b) for introduction into the polish composition, into a third phase in which the second phase of the simple emulsion is insoluble, in order to obtain a multiple, stable emulsion constituted by three phases, said third phase being soluble in the polish composition.

The emulsion may advantageously comprise an aqueous phase and an "oil" phase or "solvent" phase. Preferably, the "solvent" phase of the emulsion comprises one or more organic solvents that are slightly miscible or immiscible with water, such as $C_2$-$C_8$ alkyl acetates, for example ethyl and/or butyl acetates, traditionally used in solvent-based polish compositions.

In order to obtain stable emulsions, it is important to add at least one surfactant to at least one of the phases of the emulsion. Said surfactant or said mixture of surfactants is selected from cationic, anionic, amphoteric, or non-ionic surfactants, preferably with a low molar mass below 1000, advantageously below approximately 500. Preferably, the non-ionic surfactant has a HLB (hydrophilic lipophilic balance) in the range 0 to 20, advantageously in the range 2 to 8 for "water-in-oil" type emulsions, and advantageously in the range 12 to 16 for "oil-in-water" type emulsions.

Thus, it is possible to introduce the emulsion into the polish composition in proportions in the range 0.01% to 5% by weight, preferably in the range 0.1% to 3% by weight of said polish composition. These proportions correspond, for example, to water contents (namely less than 3%, preferably less than 1% by weight) in a solvent-based polish that are very low; compared with compositions such as those described in U.S. Pat. No. 5,102,654 (containing 5% to 15% by weight of water), while also increasing the quantity of active agent in said polish.

This means that the agent with an action on the nail can be introduced in higher concentrations than for those of the prior art, thus leading to better action of that compound at the nail surface after application of the polish composition.

In a first implementation of the method of the invention, when the polish composition is a water-based composition, the active agent is present in the hydrophobic phase of the simple emulsion or in the hydrophilic phase of the multiple emulsion.

In a second implementation of the method of the invention, when the polish composition is a composition based on solvents with a more hydrophobic nature, the active agent is present in the hydrophilic phase of the simple emulsion or in the hydrophobic phase of the multiple emulsion.

The agent with an action on the nail may be either a mineral salt or an organic molecule. If it is a mineral salt, it may be selected from halides (preferably chlorides or iodides) or sulfates, preferably aluminum, copper, magnesium, manganese, iron, potassium, calcium or sodium sulfates, or a mixture thereof. If it is an organic molecule or a mixture of organic molecules, they may be selected from vitamins such as vitamins A, B5, C, E, F, H or derivatives thereof, plant extracts, fruit extracts, algae extracts, fungus extracts or caviar extracts, aldehydes (such as citral, hexanal, etc.), vegetable oils (such as soya, castor, jojoba, walnut, olive, mongongo, sunflower seed oil, etc.), essential oils, amino acids, peptides, proteins, ceramides, allantoin and its derivatives, organosilicon derivatives, active agents obtained by fermentation, benzalkonium halides and dialkylsulfones.

Finally, the present invention also provides nail polish compositions per se, comprising a film-forming agent, advantageously obtained by the method described above in which at least one agent with an action on the nail is present in a phase that is immiscible with the solvent for said polish and/or in a phase distinct from the solvent phase of said polish, so as to be protected during storage of said polish and released in contact with the nail during application of the polish to the nail.

More particularly, in a first embodiment of the invention, the nail polish composition is a water-based composition and the active agent is present in a hydrophobic phase or in a hydrophilic phase in emulsion in a hydrophobic phase.

In a second embodiment, the nail polish composition is a composition based on solvents with a hydrophobic nature, and the active agent is present in a hydrophilic phase or in a hydrophobic phase in emulsion within a hydrophilic phase. The hydrophilic phase may then advantageously have a water content of less than 1% by weight, preferably less than 0.5% by weight.

The invention is illustrated below in non-limiting examples.

The aim of these examples was to protect the agent with an action on the nails in conventional nail polish compositions.

Two types of polish were used, water-based polish compositions (for which the major solvent is water) and organic solvent-based polish compositions.

EXAMPLE 1

Water-Soluble Mineral Active Agents

These mineral active agents are soluble in water.
The "water" phase and the "solvent" phase were prepared by mixing the following components separately, with stirring:

TABLE 1

| Constituents | Parts by weight |
|---|---|
| Water phase: | |
| Demineralized water | 68 |
| Preservative | 1 |
| Mixture of water-soluble mineral active agents | 7 |
| Total | 76 |
| Solvent phase: | |
| Nitrocellulose | 3 |
| Butyl acetate | 117 |
| Cetyl PEG/PPG-10/1 Dimethicone (HLB index = 5) | 4 |
| Total | 124 |

The mixture of mineral active agents of the "water" phase in this example was a mixture comprising:

5 parts by weight of a multimineral complex II supplied by Procital and containing Al, Mg, Mn, Na, K, Zn chlorides, copper sulfate, and lysine; and 2 parts by weight of Atoligomer supplied by Codif, which is a concentrate of seawater salts from which sodium has been removed.

The water phase was introduced into the solvent phase with stirring, then the mixture was stirred for 10 minutes at 1500 rpm [revolutions per minute].

The emulsion obtained was white and stable for several months. This emulsion was then introduced, with stirring, in a proportion of 1% by weight, into a transparent nitrocellulose polish the composition of which is detailed in Table 2 below.

TABLE 2

| Polish constituents | % by weight |
|---|---|
| Ethyl acetate | 40 |
| Butyl acetate | 24 |
| Nitrocellulose (30% in isopropyl alcohol) | 17 |
| Polyester resin | 11.5 |
| Acetyl tributyl citrate | 7.5 |
| Total | 100 |

This example shows how it is possible to incorporate water-soluble salts into a nitrocellulose polish based on an organic solvent with a reduced water content (0.4% by weight of polish). These oligoelements are necessary for good nail growth. They are released onto the nail after the polish has been applied thereto and dried.

Incorporating a water-in-solvent emulsion into the polish of Table 2 does not modify either the transparency or the conventional properties of this type of polish, nor its pH. Table 3 below presents the results observed. It was not obvious that a stable emulsion could be incorporated in this manner into a liquid composition having a large solvent fraction.

TABLE 3

| Properties of polish | Comprising 1% emulsion | No emulsion |
|---|---|---|
| Hardness | 263 | 210-280 |
| Gloss | 90.7 | 85-92 |
| Glass adhesion | 0-1 | 0-1 |
| Drying time | 3 min 15 s | 2 min 30 to 4 min 30 s |
| Water content | 0.57% | 0.3%-0.5% |
| Dry extract | 27.32% | 26-28% |
| Viscosity (60 rpm) | 250 mPa · s | 140-280 mPa · s |

The physical characteristics of the polish were tested using the following methods:

the gloss was measured with a Minolta 268 gloss meter (angle of incidence 60°) for application onto a LENETA type card, and expressed in terms of a scale of up to 100;

the hardness was measured using a "Persoz" pendulum on a dry film formed by applying a 100 μm [micrometer] thick layer of polish to a glass plate, after drying overnight at ambient temperature (20° C.) (the values obtained are expressed in seconds);

glass adhesion: the film of polish formed on glass was scored in a cross-hatched pattern with a SHEEN 750/1 type six-bladed comb. An adhesive tape applied to the scoremarks was torn off and it was observed that less than 5% of the surface of the film had been torn off, corresponding to good adhesion expressed as a value in the range 0 to 1 (on a scale of 5);

the viscosity was measured using a Brookfield LVT viscosimeter with needle No. 3 at 25° C. at 6 rpm or at 60 rpm for one minute; this meant that the ability of the polish to spread well could be assessed.

EXAMPLE 2

Calcium Pantothenate in Solution in Water

Calcium pantothenate (a vitamin B5 derivative) is important in strengthening nails (brittle nails) by a healing action. However, it is only very slightly soluble in the organic solvents normally employed in nail polishes. Nevertheless, it has been shown to be highly soluble in water, and it may be dissolved in water in high concentrations.

Thus, the compound was dissolved in demineralized water and a solvent phase was prepared separately. The compositions of the two phases were as follows (Table 4):

TABLE 4

| Constituents | Parts by weight |
| --- | --- |
| Water phase: | |
| Demineralized water | 61 |
| Calcium pantothenate | 15 |
| Total | 76 |
| Solvent phase: | |
| Nitrocellulose | 3 |
| Butyl acetate | 116 |
| Cetyl PEG/PPG-10/1 Dimethicone (HLB index = 5) | 5 |
| Total | 124 |

The water phase was introduced into the solvent phase with stirring, then the mixture was stirred for 10 minutes at 1500 rpm.

The water-in-solvent emulsion obtained was white and stable at ambient temperature (approximately 20° C. to 25° C.) for several months. This simple two-phase emulsion was then introduced, with stirring, in a proportion of 1% by weight, into a nitrocellulose polish the composition of which is detailed in Table 5 below.

The polish was a thixotropic base slightly pigmented with white:

TABLE 5

| Polish constituents | % by weight |
| --- | --- |
| Ethyl acetate | 18.7 |
| Butyl acetate | 38 |
| Nitrocellulose (30% in isopropyl alcohol IPA) | 18 |
| Polyester resins | 12 |
| Acetyl tributylcitrate | 8 |
| Styrene acrylic resin | 2 |
| Stearalkonium bentonite | 1.3 |
| Titanium oxide | 2 |
| Total | 100 |

Calcium pantothenate has a tendency to turn nitrocellulose polishes yellow; however, it was surprisingly observed that when it was introduced in the form of an emulsion, this yellowing effect was diminished.

Table 6 below summarizes the properties of this polish base including 1% of the water-in-solvent emulsion described above.

TABLE 6

| Properties of polish | Comprising 1% emulsion | No emulsion |
| --- | --- | --- |
| Hardness | 172 | 200 |
| Gloss | 88.9 | 88.4 |
| Glass adhesion | 0-1 | 0-1 |
| Drying time | 4 min | 3 min 45 s |
| Water content | 0.60% | 0.40% |
| Dry extract | 31.09% | 31.50% |
| Viscosity (6-60-6 rpm) | 1300/546/880 mPa · s | 2120/670/1200 mPa · s |

In this example, adding the emulsion caused the hardness to drop (it was initially close to 200). It was observed that the calcium pantothenate introduced in this manner had a less yellowing effect on the polish than when it was introduced in the form of an alcoholic solution.

The whiteness index (0=black and 100=totally white) was measured spectrophotometrically using Leneta plates onto which a layer of polish had been applied. The results were as follows:

Reference Polish:
  the whiteness index was 79.99 at t=0, then after one week at 55° C.: the whiteness index was 77.30 (i.e. a reduction of 3.36%).

Polish with Alcoholic Solution of Calcium Pantothenate:
  the whiteness index was 80.07, then 68.51 after one week (corresponding to −14.43%).

Polish with Emulsion of Calcium Pantothenate:
  79.84 then 68.89 (−13.71%).

At the same time, another test was carried out with another yellowing active agent (D-panthenol), which produced the same results: when added in the form of an emulsion of D-panthenol, there was less yellowing than when it was added in the form of an alcoholic solution. These active agents thus appear to be protected from degradation when they are in the form of an emulsion.

EXAMPLE 3

Vitamin E Acetate

This compound was prepared in order to form an "oil-in-water" type emulsion then introduced into a water-based polish with stirring.

The composition of the two phases of the emulsion is shown in Table 7.

TABLE 7

| Constituents | Parts by weight |
| --- | --- |
| Oily phase: | |
| Vitamin E acetate | 40 |
| Modified non-ionic fatty acid derivative | 10 |
| Total | 50 |
| Water phase: | |
| Demineralized water | 49 |
| Preservative | 1 |
| Total | 50 |

The surfactant was an ethoxylated fatty acid derivative supplied under the name Tego Dispers 740 W.

The oily phase was introduced into the water phase with stirring.

The emulsion obtained was milky and stable for several months at ambient temperature.

This emulsion was then introduced, with stirring, into an aqueous polish phase in proportions of 0.5% by weight of polish the composition of which is shown in Table 8 below.

TABLE 8

| Polish constituents | % by weight |
|---|---|
| Film-forming agent: styrene/acrylic copolymers in emulsion | 76 |
| Coalescing agent | 4 |
| Plasticizer | 2 |
| Magnesium and sodium silicate | 0.7 |
| Preservative | 0.5 |
| Organic thickening agent | 0.5 |
| Siliconized surfactant and slip agent | 0.5 |
| Pigments | 0.6 |
| Mica titanium | 2 |
| Demineralized water | 13.2 |
| Total | 100 |

In this example, the emulsion form meant that vitamin E could be added to a product in an aqueous phase. When it is to be incorporated directly into the water-based polish, it was observed that it was completely immiscible, resulting in it being impossible to apply to the nail as mini-droplets of oil.

In contrast, the polish applied with the vitamin E acetate in emulsion forms a homogeneous, regular film on the nail.

EXAMPLE 4

Multiple Emulsion of Vitamin E Acetate

The "oil-in-water" emulsion of Example 3 was then emulsified in a new solvent medium comprising a mixture of surfactants.

The emulsion obtained, which became an emulsion of the "oil-in-water-in-solvent" type, had the following composition (Table 9).

TABLE 9

| Constituents | Parts by weight |
|---|---|
| Solvent phase: | |
| Butyl acetate | 36 |
| Ethyl acetate | 25 |
| Nitrocellulose | 10 |
| Cetyl PEG/PPG-10/1 Dimethicone (HLB index = 5) | 0.6 |
| Sorbitan Sesquioleate (HLB index = 3.7) | 0.4 |
| Total | 72.0 |
| Oil-in-water emulsion: | |
| Emulsion of Example 3 | 28 |

The oil-in-water phase introduced into the solvent phase with stirring resulted in a multiple emulsion that was white and stable over several months.

This emulsion could then be introduced, with stirring, into a solvent-based polish in an amount of 1% by weight in the polish presented in Table 10.

TABLE 10

| Constituents of solvent based polish | % by weight |
|---|---|
| Solvents | |
| Butyl acetate | 40 |
| Ethyl acetate | 29.5 |
| Isopropanol | 4.5 |
| Nitrocellulose | 10.5 |
| Acetyl tributyl citrate (ATC) | 6 |
| Polyester resin | 4 |
| Acrylic resin | 1.5 |
| Stearalkonium hectorite | 1 |
| Pigment | 3 |
| Total | 100 |

In all of the above-mentioned examples, the emulsions remained stable when stored between 20° C. and 25° C. away from the light.

The invention claimed is:

1. A method of incorporating an active agent into a nail polish composition comprising a film-forming agent, the method comprising the following steps:
   a) preparing an oil-in-water or water-in-oil type emulsion by bringing a first phase constituted by said active agent, or a solution comprising said active agent dissolved in it, into contact, with stirring, with a second phase in which the active agent is insoluble or slightly soluble, in the presence of at least one surfactant, and obtaining a simple, stable emulsion of two phases, a first, discontinuous phase being present in the form of droplets in a second, continuous phase, said second phase being soluble in the nail polish composition; and
   b) introducing, with stirring, said emulsion into the nail polish composition in proportions in the range 0.01% to 5% of the composition weight.

2. The method according to claim 1, wherein the emulsion is introduced into the nail polish composition in proportions in the range 0.1% to 3% of said polish composition weight.

3. The method according to claim 1, further comprising a step a) bis in which the simple emulsion obtained at the end of step a) is incorporated, with stirring, before step b) into a third phase in which the second phase of the simple emulsion is insoluble, in order to obtain a multiple, stable emulsion of three phases, said third phase being soluble in the nail polish composition.

4. The method according to claim 1, wherein the at least one surfactant is selected from cationic, anionic, amphoteric and non-ionic surfactants, or a mixture thereof.

5. The method according to claim 1, wherein the at least one surfactant has a molar mass of less than 1000.

6. The method according to claim 4, wherein the non-ionic surfactant has a HLB (hydrophilic lipophilic balance) in the range 0 to 20.

7. The method according to claim 3, wherein the nail polish composition is a water-based composition, and the active agent is present in the hydrophobic phase of the simple emulsion or in the hydrophilic phase of the multiple emulsion.

8. The method according to claim 3, wherein when the nail polish composition is a composition based on solvents with a hydrophobic nature, the active agent is present in the hydrophilic phase of the simple emulsion or in the hydrophobic phase of the multiple emulsion.

9. The method according to claim 1, wherein the active agent is a mineral salt selected from halides, preferably chlorides or iodides, or sulfates, preferably aluminum, copper, magnesium, manganese, iron, potassium, calcium or sodium sulfates, or a mixture thereof.

10. The method according to claim 1, wherein the active agent is an organic molecule or a mixture of organic molecules selected from: vitamins or derivatives thereof, plant extracts, fruit extracts, algae extracts, fungus extracts or caviar extracts, aldehydes, vegetable oils, essential oils, amino acids, peptides, proteins, ceramides, allantoin and its derivatives, organosilicon derivatives, active agents obtained by fermentation, and dialkylsulfones.

11. A nail polish composition comprising a film-forming agent, obtained by the method according to claim 1, wherein at least one active agent is present in a phase that is immiscible with the solvent for said polish and/or in a phase distinct from the solvent phase of said polish, so as to be protected during storage of said polish and released when in contact with the nail during application of the polish to the nail.

12. The nail polish composition according to claim 11, wherein when said composition is a water-based composition, the active agent is present in a hydrophobic phase, or in a hydrophilic phase in emulsion within a hydrophobic phase.

13. The nail polish composition according to claim 11, wherein when the composition is based on solvents with a hydrophobic nature, the active agent is present in a hydrophilic phase, or in a hydrophobic phase in emulsion within a hydrophilic phase.

14. The nail polish composition according to claim 13, wherein the hydrophilic phase has a water content of below 1% by weight, preferably below 0.5% by weight.

15. The method according to claim 2, further comprising a step a) bis in which the simple emulsion obtained at the end of step a) is incorporated, with stirring, before step b), into a third phase in which the second phase of the simple emulsion is insoluble, in order to obtain a multiple, stable emulsion of three phases, said third phase being soluble in the nail polish composition.

16. The method according to claim 5, wherein the nonionic surfactant has a HLB (hydrophilic lipophilic balance) in the range 0 to 20.

* * * * *